United States Patent [19]
Kato et al.

[11] Patent Number: 5,948,963
[45] Date of Patent: Sep. 7, 1999

[54] GAS SENSOR

[75] Inventors: Nobuhide Kato, Ama-gun; Nobukazu Ikoma; Yasuhiko Hamada, both of Nagoya, all of Japan

[73] Assignee: NGK Insulators, Ltd., Japan

[21] Appl. No.: 09/079,187

[22] Filed: May 15, 1998

[30] Foreign Application Priority Data

May 20, 1997 [JP] Japan ..................................... 9-130154

[51] Int. Cl.⁶ .......................... G01N 31/00; G01N 27/28; H01C 7/00; G01M 15/00
[52] U.S. Cl. .......................... 73/23.2; 73/31.05; 73/23.32; 422/83; 204/428; 204/245
[58] Field of Search ................................ 73/23.2, 31.05, 73/23.32, 64.47; 422/83, 88, 94; 338/34; 204/428, 279, 245

[56] References Cited

U.S. PATENT DOCUMENTS

| | | | |
|---|---|---|---|
| 3,187,562 | 6/1965 | Rolfson | 73/53 |
| 3,590,634 | 7/1971 | Pasternak et al. | 73/159 |
| 4,028,931 | 6/1977 | Bisera et al. | 73/64.3 |
| 4,125,347 | 11/1978 | Bode et al. | 23/232 E |
| 4,570,479 | 2/1986 | Sakurai et al. | 73/116 |
| 4,611,562 | 9/1986 | Nakano et al. | 123/440 |
| 4,633,704 | 1/1987 | Tantram et al. | 73/23 |
| 4,663,958 | 5/1987 | Matthiessen | 73/1 G |
| 4,745,796 | 5/1988 | Abdelrahman et al. | 73/26 |
| 4,833,909 | 5/1989 | Matthiessen | 73/23 |
| 5,039,972 | 8/1991 | Kato et al. | 338/34 |
| 5,211,055 | 5/1993 | Steudle et al. | 73/64.47 |
| 5,228,975 | 7/1993 | Yamada et al. | 204/424 |
| 5,321,971 | 6/1994 | Hobbs et al. | 73/23.2 |
| 5,520,209 | 5/1996 | Goins et al. | 137/246 |
| 5,627,306 | 5/1997 | Yamauchi et al. | 73/23.2 |
| 5,644,069 | 7/1997 | Liu et al. | 73/23.2 |
| 5,763,763 | 6/1998 | Kato et al. | 73/23.2 |
| 5,777,208 | 7/1998 | Martell et al. | 73/31.06 |
| 5,814,281 | 9/1998 | Williams et al. | 422/88 |
| 5,821,401 | 10/1998 | Awarzamani et al. | 73/23.32 |

FOREIGN PATENT DOCUMENTS

| | | |
|---|---|---|
| 0 520 528 A1 | 12/1992 | European Pat. Off. . |
| 43 42 73 A1 | 2/1995 | Germany . |
| 2-146362 | 12/1990 | Japan . |
| 5-26842 | 2/1993 | Japan . |
| 6-37325 | 9/1994 | Japan . |
| 6-37326 | 9/1994 | Japan . |
| 8-247995 | 9/1996 | Japan . |
| 8-274476 | 10/1996 | Japan . |

*Primary Examiner*—Hezron Williams
*Assistant Examiner*—J. David Wiggins
*Attorney, Agent, or Firm*—Parkhurst & Wendel, LLP

[57] ABSTRACT

Disclosed is a gas sensor comprising a sensor element for measuring a predetermined gas component contained in an introduced measurement gas, and a protective cover arranged to surround a forward end of the sensor element; the gas sensor including the sensor element having a gas-introducing port which is disposed at a forward end surface thereof for introducing the measurement gas thereinto; and the protective cover comprising an inner protective cover and an outer protective cover. The inner protective cover is provided with an opening section which makes communication with the gas-introducing port. An inner protective cover space, which is formed between the inner protective cover and the sensor element, is isolated from a communication passage which makes communication from the opening section of the inner protective cover to the gas-introducing port of the sensor element so that the measurement gas principally diffuses and flows from the opening section into the gas-introducing port of the sensor element. Accordingly, it is possible to simultaneously solve the element temperature drop and the crack formation caused by condensed water, and highly accurately measure the predetermined gas component.

15 Claims, 11 Drawing Sheets

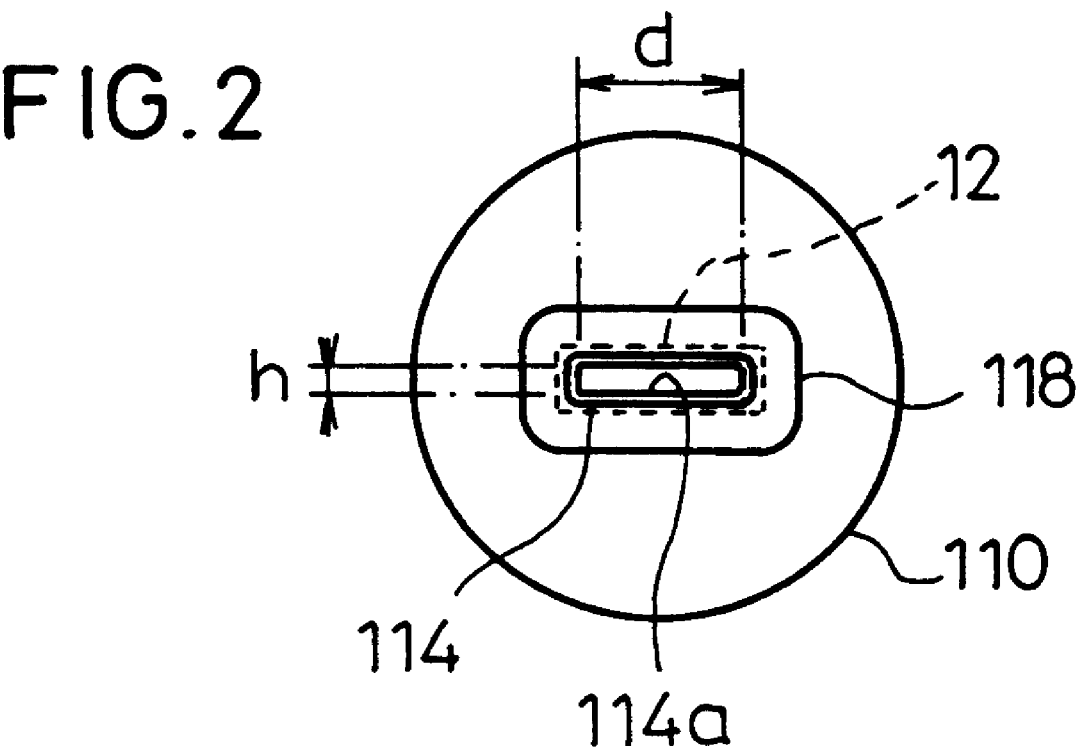

GAS SENSOR

BACKGROUND OF THE INVENTION

1. Field of the Invention

The present invention relates to a gas sensor for measuring gas components such as NO, $NO_2$, $SO_2$, $CO_2$, and $H_2O$ contained in, for example, atmospheric air and exhaust gas discharged from vehicles or automobiles. In particular, the present invention relates to a structure of a protective cover which is arranged to surround a sensor element.

2. Description of the Related Art

A variety of gas sensors have been suggested and practically used until the present, including, for example, oxygen sensors, NOx sensors (see Japanese Laid-Open Patent Publication No. 8-271476), and HC sensors (see Japanese Laid-Open Patent Publication No. 8-247995) based on the use of oxygen ion conductors; hydrogen sensors and $H_2O$ sensors based on the use of proton ion conductors; and oxygen sensors and various gas sensors based on the use of oxide semiconductors such as $SnO_2$ and $TiO_2$.

Among the gas sensors described above, the oxygen sensor based on the use of $ZrO_2$ and the oxygen sensor based on the use of $TiO_2$ are widely used for A/F control or for controlling the oxygen concentration in exhaust gas discharged from vehicles or automobiles, because they still maintain stable performance even in an environment of automobile exhaust gas.

The NOx sensor based on the use of $ZrO_2$ has also arrived at the stage of practical use for controlling NOx for automobiles.

In general, the gas sensor based on the use of $ZrO_2$ contains a heater. An electric power is applied to a heater simultaneously with the start of the engine. The temperature of the sensor element is raised earlier than the temperature of exhaust gas to be raised, and it arrives at an operation temperature.

On the other hand, condensed water is produced during the starting operation of the engine. The amount of production of the condensed water decreases as the temperature of exhaust gas is raised, and the condensed water gradually disappears. Therefore, when the sensor element is sufficiently heated during the time zone of condensed water production, a thermal shock may be exerted on the sensor element due to adhesion of the condensed water, resulting in occurrence of cracks.

Especially, the gas sensor, in which the heater and the sensor element are integrated into one unit, has suffered from a drawback that the crack highly probably occurs, because the temperature of the sensor is quickly raised, and the sensor is sufficiently heated to a high temperature during the time zone of condensed water production.

In order to dissolve the drawback described above, a protective cover has been suggested as a countermeasure against condensed water for the oxygen sensor of the type containing a heater therein, and it is practically used at present (for example, see Japanese Laid-Open Patent Publication No. 5-26842).

However, in recent years, since these gas sensors come to be attached downstream of the three way catalyst, involves a problem that the time zone of condensed water production is markedly prolonged, and the probability of crack formation in the sensor element is increased even when the foregoing protective cover is used, as compared with the conventional gas sensor which is attached upstream of the three way catalyst.

Further, those based on the use of the oxygen pump function, such as the NOx sensor, are heated to a temperature not lower than 700° C. in order to effectively operate the oxygen pump. Therefore, they involve a problem that the thermal shock exerted thereon upon contact with condensed water is by far greater than that exerted on the oxygen sensor of the heating type, and the probability of crack formation is high.

Furthermore, in the case of the gas sensor based on the use of the sensor element which should be heated to a high temperature as described above, the low temperature environment is dominant as the sensor is attached to a more downstream position in an exhaust pipe. As a result, an inconvenience arises in that the sensor element tends to be cooled, and the oxygen pump is not operated effectively. Especially, this problem is serious for the diesel engine and the lean burn engine, because the exhaust gas temperature is low.

SUMMARY OF THE INVENTION

The present invention has been made taking the foregoing problems into consideration, an object of which is to provide a gas sensor which makes it possible to simultaneously solve the element temperature drop and the crack formation caused by condensed water, and highly accurately measure a predetermined gas component.

According to the present invention, there is provided a gas sensor comprising a sensor element for measuring a predetermined gas component contained in an introduced measurement gas, and a protective cover arranged to surround the sensor element; the gas sensor including the sensor element having a gas-introducing port which is disposed at a forward end surface thereof for introducing the measurement gas thereinto; the protective cover having an opening section which makes communication with the gas-introducing port; and a protective cover space formed between the protective cover and the sensor element, the protective cover space being isolated from a communication passage which makes communication from the opening section of the protective cover to the gas-introducing port of the sensor element; wherein the measurement gas principally diffuses and flows from the opening section into the gas-introducing port of the sensor element.

According to the present invention, it is difficult for condensed water to make invasion. Even if condensed water makes invasion, the size of water droplets is extremely small. Therefore, even if condensed water contacts with the forward end of the sensor element, the thermal shock exerted thereby is extremely small. Accordingly, no crack is formed at the forward end of the sensor element.

Owing to the fact that the protective cover space is isolated from the communication passage, the measurement gas, which is allowed to diffuse and flow from the opening section to the sensor element, does not enter the protective cover space. Accordingly, it is possible for the sensor element to measure the concentration of the measurement gas with good response performance.

Further, the gas sensor is structured such that the gas-introducing port is disposed at the forward end of the sensor element, and the opening section of the protective cover directly communicates with the gas-introducing port of the sensor element. Therefore, the sensor element is not easily cooled, and the probability of adhesion of condensed water to the sensor element is extremely small.

Even if oil combustion waste and carbon, which are contained in exhaust gas, adhere to the opening section to increase the gas diffusion resistance of the opening section, it is possible to suppress the decrease in sensitivity and the decrease in response performance to the minimum, because the gas diffusion resistance of the opening section is set to be sufficiently low as compared with the gas diffusion resistance of the sensor element.

As for the gas sensor constructed as described above, assuming that a gas diffusion resistance of the communication passages is D1, and a gas diffusion resistance from the protective cover space to the communication passage is D2, it is preferable that a ratio D1/D2 between the gas diffusion resistances (hereinafter referred to as "isolation gas diffusion resistance ratio") is not more than 1/5. In this embodiment, the diffusion of gas into the protective cover space is suppressed, and hence it is possible to greatly improve the delay of response in the sensor element.

It is preferable for the gas sensor constructed as described above that a hole (side hole or bottom hole) for making communication for at least the measurement gas with the protective cover space is provided through a side surface and/or a bottom surface of the protective cover. In this embodiment, even if the isolation gas diffusion resistance ratio is not less than 1/5, it is possible to improve the delay of response. When the isolation gas diffusion resistance ratio is not more than 1/5, more quick response is obtained. However, since the side hole or the bottom hole may cause the element temperature drop and the increase in probability of adhesion of condensed water, it is preferable to allow the hole to have a small diameter as far as possible. The hole may be provided either through the side surface or through the bottom surface of the protective cover. Alternatively, the hole may be provided through both of the side surface and the bottom surface of the protective cover. The hole preferably has a diameter of not more than 1 mm.

It is preferable for the gas sensor constructed as described above that the end surface of the sensor element abuts against the protective cover. In this embodiment, the protective cover space is more reliably isolated from the communication passage.

It is preferable for the gas sensor constructed as described above that the isolation space is filled with a filler. In order to lower the isolation gas diffusion resistance ratio, the gap is preferably filled with a heat-resistant filler such as glass, ceramic cement, glass wool, and metal mesh (obtained by pressing and hardening metal wire).

The gas sensor constructed as described above may further comprises an outer protective cover disposed to surround the protective cover and provided with at least a gas-introducing hole. Accordingly, the internal protective cover is not directly exposed to the measurement gas, and this arrangement is extremely effective as a countermeasure against the element temperature drop.

In another embodiment, a gas discharge hole for the measurement gas may be provided through a bottom of the outer protective cover. By doing so, the measurement gas does not directly flow toward the opening section. Therefore, condensed water hardly contacts with the opening section, and adhesion of oil combustion waste or the like is decreased.

It is preferable that a plurality of gas discharge holes each having a diameter of not more than 2 mm are provided through the bottom of the outer protective cover. More preferably, the gas discharge hole is provided at a position at which it does not oppose to the opening section. Accordingly, scattered water droplets are decreased, and the probability of crack formation is decreased. In this embodiment, the provision of the gas discharge hole at the position at which it does not oppose to the opening section further decreases the probability that condensed water will move toward the opening section.

It is preferable for the gas sensor constructed as described above that a gas diffusion resistance of the opening section is not more than 1/10 of a gas diffusion resistance of the sensor element. In this embodiment, even when oil combustion waste or the like adheres to the opening section, it is possible to decrease the influence exerted thereby on the sensitivity and the decrease in response performance.

It is preferable for the gas sensor constructed as described above that a length of the opening section in a direction to extend toward the sensor element is not less than 1.5-fold of an aperture width of the opening section. In this embodiment, it is possible to greatly decrease the probability that scattered water droplets will contact with the sensor element. Various configurations may be conceived for the shape of the aperture of the opening section, including, for example, slit-shaped, elliptic, and circular configurations. When the aperture has a slit-shaped configuration, it is desirable that the slid width is not more than 1 mm. By doing so, scattered water droplets are decreased, and the thermal shock exerted on the sensor element is simultaneously decreased. Thus, it is possible to further decrease the probability of crack formation.

It is preferable for the gas sensor constructed as described above that the opening section is filled with a porous material. In this embodiment, the opening section may be filled with, for example, porous metal, metal mesh, porous ceramic, and glass wool. Accordingly, it is possible to further decrease the probability that condensed water will contact with the sensor element. Therefore, the use of the filler is especially effective when the opening section has a large aperture width.

It is preferable for the gas sensor constructed as described above that the opening section is composed of a member which is different from that for the protective cover. In this embodiment, it is possible to easily dissolve any positional dispersion of the sensor element. Further, it is possible to set, for example, the height of the opening section and the aperture area without restraint. Thus, the degree of freedom of design is increased for the opening section. For example, when the aperture area at the inlet portion of the opening section is increased, and the height of the opening section is increased, then it is possible to increase the height without increasing the gas diffusion resistance. Thus, it is possible to further decrease the probability of adhesion of condensed water. Furthermore, it is possible to design and manufacture the gas sensor to give a sufficiently large value of the gas diffusion resistance of the isolation space (the gap between the sensor element and the opening section).

It is preferable for the gas sensor constructed as described above that a recess is provided at a bottom of the protective cover, and the opening section is provided at the recess. This embodiment has the following feature. That is, the length of the inflow passage of the measurement gas is increased, and hence condensed water scarcely makes contact. Further, the opening section hardly suffers from adhesion of particles such as oil combustion waste, because the opening section is arranged at the deep portion of the recess.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 2 shows a magnified view of principal parts illustrating a magnified opening section shown in FIG. 1B;

DESCRIPTION OF THE PREFERRED EMBODIMENTS

Explanation will be made below with reference to FIGS. 1A to 17 for several illustrative embodiments in which the gas sensor according to the present invention is applied to gas sensors for measuring gas components such as NO, $NO_2$, $SO_2$, $CO_2$, and $H_2O$ contained, for example, in atmospheric air and exhaust gas discharged from vehicles or automobiles.

Figure 1A:
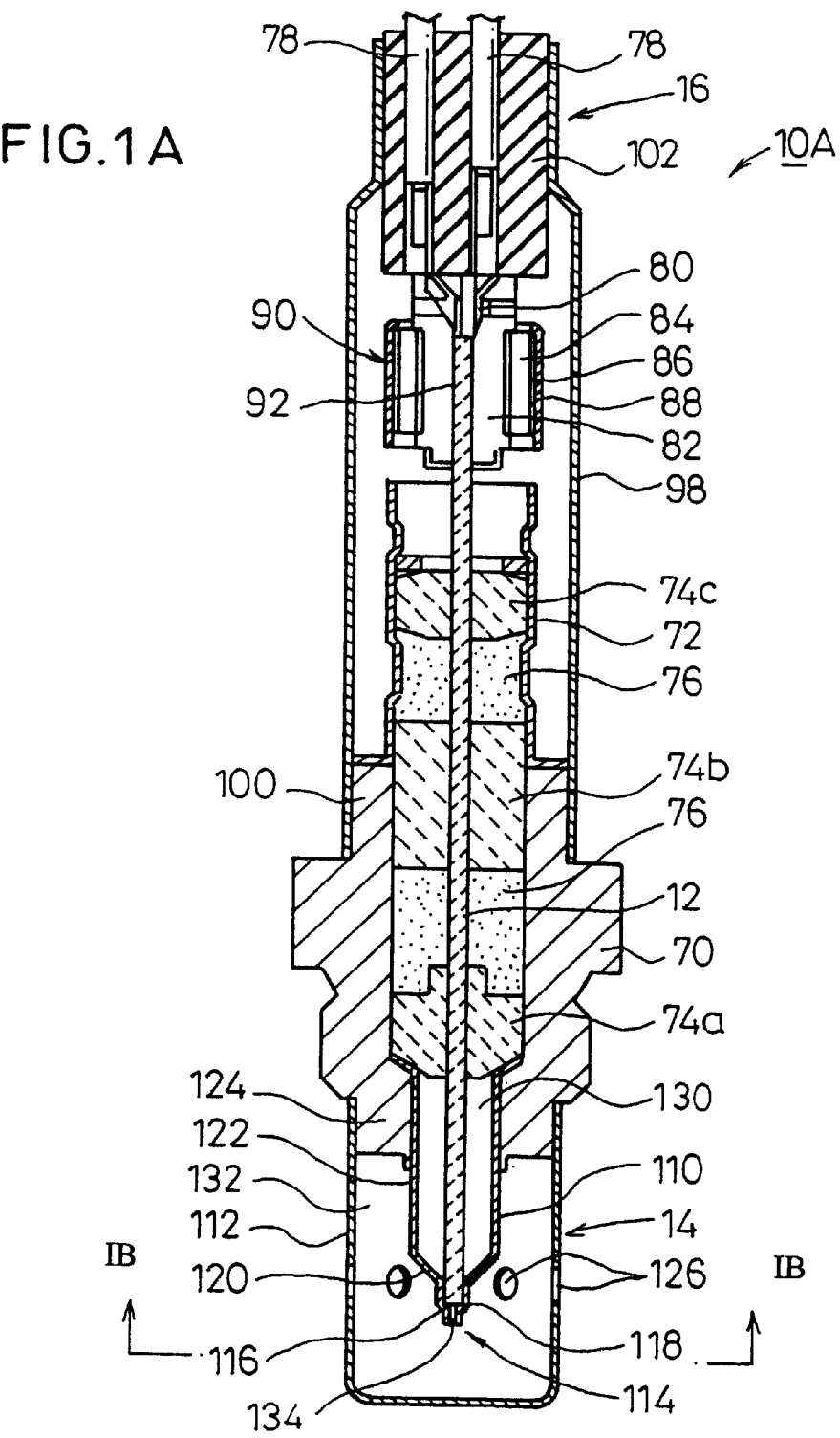
FIG. 1A shows a longitudinal sectional view illustrating an arrangement of a gas sensor according to a first embodiment.

As shown in FIG. 1A, a gas sensor 10A according to a first embodiment comprises a sensor element 12 for measuring a predetermined gas component such as NOx contained in an introduced measurement gas (exhaust gas), a protective cover 14 arranged to surround a forward end of the sensor element 12, and a sensor assembly 16 arranged to surround the entire sensor element 12 except for the forward end and constructed to make electric connection to the outside.

Figure 3:
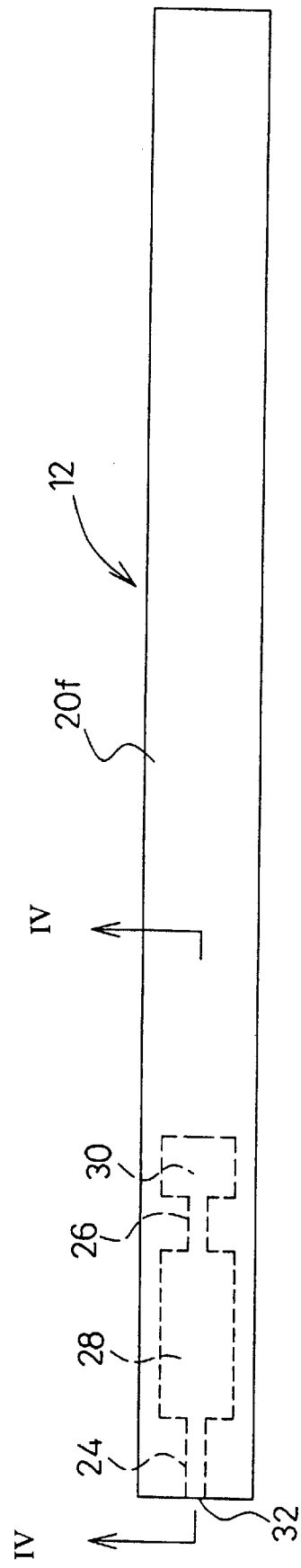
FIG. 3 shows a plan view illustrating an arrangement of a gas sensor element.
Figure 4:
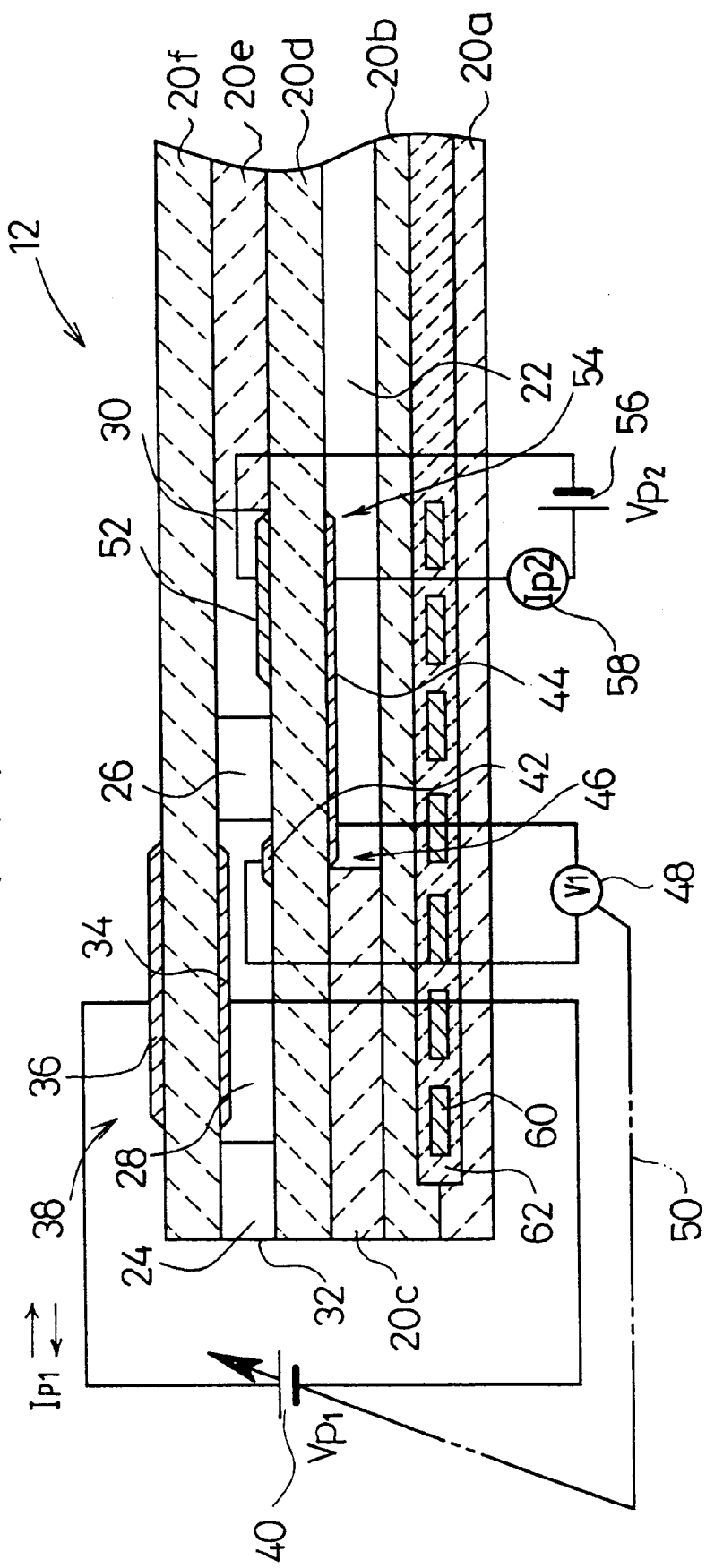
FIG. 4 shows a sectional view taken along a line IV—IV shown in FIG. 3.

As shown in FIGS. 3 and 4, the sensor element 12 is generally constructed to have a lengthy plate-shaped configuration comprising, for example, six stacked solid electrolyte layers 20a to 20f composed of ceramics based on the use of oxygen ion-conductive solid electrolytes such as $ZrO_2$. First and second layers from the bottom are designated as first and second substrate layers 20a, 20b respectively. Third and fifth layers from the bottom are designated as first and second spacer layers 20c, 20e respectively. Fourth and sixth layers from the bottom are designated as first and second solid electrolyte layers 20d, 20f respectively.

Specifically, the first spacer layer 20c is stacked on the second substrate layer 20b. The first solid electrolyte layer 20d, the second spacer layer 20e, and the second solid electrolyte layer 20f are successively stacked on the first spacer layer 20c.

A space (reference gas-introducing space) 22, into which a reference gas such as atmospheric air to be used as a reference for measuring oxides is introduced, is formed between the second substrate layer 20b and the first solid electrolyte layer 20d, the space 22 being comparted by a lower surface of the first solid electrolyte layer 20d, an upper surface of the second substrate layer 20b, and side surfaces of the first spacer layer 20c.

The second spacer layer 20e is interposed between the first and second solid electrolyte layers 20d, 20f. First and second diffusion rate-determining sections 24, 26 are also interposed between the first and second solid electrolyte layers 20d, 20f.

A first chamber 28 for adjusting the partial pressure of oxygen in the measurement gas is formed and comparted by a lower surface of the second solid electrolyte layer 20f, side surfaces of the first and second diffusion rate-determining sections 24, 26, and an upper surface of the first solid electrolyte layer 20d. A second chamber 30 for finely adjusting the partial pressure of oxygen in the measurement gas and measuring oxides, for example, nitrogen oxides (NOx) in the measurement gas is formed and comparted by a lower surface of the second solid electrolyte layer 20f, a side surface of the second diffusion rate-determining section 26, a side surface of the second spacer layer 20e, and an upper surface of the first solid electrolyte layer 20d.

A gas-introducing port 32 for introducing the measurement gas into the first chamber 28 is provided at an end surface of the second spacer layer 20e, of the forward end surface of the sensor element 12. Therefore, the external space communicates with the first chamber 28 via the gas-introducing port 32 and the first diffusion-rate determining section 24, and the first chamber 28 communicates with the second chamber 30 via the second diffusion rate-determining section 26.

The first and second diffusion-rate determining sections 24, 26 give predetermined diffusion resistances to the measurement gas to be introduced into the first and second chambers 28, 30 respectively. Each of the first and second diffusion-rate determining sections 24, 26 can be formed as a passage composed of, for example, a porous material (for example, a porous compact composed of $ZrO_2$ or the like), or a small hole having a predetermined cross-sectional area so that the measurement gas may be introduced. Alternatively, each of the first and second diffusion-rate determining sections 24, 26 may be constructed by a gap layer or a porous layer produced by printing. In this embodiment, the comparative magnitude does not matter between the respective diffusion resistances of the first and second diffusion rate-determining sections 24, 26. However, it is preferable that the diffusion resistance of the second diffusion rate-determining section 26 is larger than that of the first diffusion rate-determining section 24.

The atmosphere in the first chamber 28 is introduced into the second chamber 30 under the predetermined diffusion resistance via the second diffusion rate-determining section 26.

An inner pumping electrode 34 having a substantially rectangular planar configuration and composed of a porous cermet electrode is formed on an entire lower surface portion for forming the first chamber 28, of the lower surface of the second solid electrolyte layer 20f. An outer pumping electrode 36 is formed on a portion corresponding to the inner pumping electrode 34, of the upper surface of the second solid electrolyte layer 20f. An electrochemical pumping cell, i.e., a main pumping cell 38 is constructed by the inner pumping electrode 34, the outer pumping electrode 36, and the second solid electrolyte layer 20f interposed between the both electrodes 34, 36.

A desired control voltage (pumping voltage) Vp1 is applied between the inner pumping electrode 34 and the outer pumping electrode 36 of the main pumping cell 38 by the aid of an external variable power source 40 to allow a pumping current Ip1 to flow in a positive direction or in a negative direction between the outer pumping electrode 36 and the inner pumping electrode 34. Thus, the oxygen in the atmosphere in the first chamber 28 can be pumped out to the external space, or the oxygen in the external space can be pumped into the first chamber 28.

A measuring electrode 42 having a substantially rectangular planar configuration and composed of a porous cermet electrode is formed in the close vicinity of the second diffusion rate-determining section 26 on an upper surface portion for forming the first chamber 28, of the upper surface of the first solid electrolyte layer 20d. A reference electrode 44 is formed on a lower surface portion exposed to the reference gas-introducing space 22, of the lower surface of the first solid electrolyte layer 20d. An electrochemical sensor cell, i.e., a controlling oxygen partial pressure-measuring cell 46 is constructed by the measuring electrode 42, the reference electrode 44, and the first solid electrolyte layer 20d.

The controlling oxygen partial pressure-measuring cell 46 is operated as follows. That is, an electromotive force is generated between the measuring electrode 42 and the reference electrode 44 on the basis of a difference in oxygen concentration between the atmosphere in the first chamber 28 and the reference gas (atmospheric air) in the reference gas-introducing space 22. The partial pressure of oxygen in the atmosphere in the first chamber 28 can be detected by measuring the electromotive force by the aid of a voltmeter 48.

That is, the voltage V1 generated between the reference electrode 44 and the measuring electrode 42 is an electromotive force of the oxygen concentration cell generated on the basis of the difference between the partial pressure of oxygen of the reference gas introduced into the reference gas-introducing space 22 and the partial pressure of oxygen of the measurement gas in the first chamber 28. The voltage V1 has the following relationship known as the Nernst's equation.

$$V1 = RT/4F \cdot \ln(P_1(O_2)/P_0(O_2))$$

R: gas constant;
T: absolute temperature;
F: Faraday constant;
$P_1(O_2)$: partial pressure of oxygen in the first chamber 28;
$P_0(O_2)$: partial pressure of oxygen in the reference gas.

Therefore, the partial pressure of oxygen in the first chamber 28 can be detected by measuring the voltage V1 generated on the basis of the Nernst's equation, by using the voltmeter 48. The detected value of the partial pressure of oxygen is used to control the pumping voltage Vp1 of the variable power source 40 by the aid of a feedback control system 50. Specifically, the pumping operation effected by the main pumping cell 38 is controlled so that the partial pressure of oxygen in the atmosphere in the first chamber 28 has a predetermined value which is sufficiently low to control the partial pressure of oxygen in the second chamber 30 in the next step.

Each of the inner pumping electrode 34 and the outer pumping electrode 36 of the main pumping cell 38 and the measuring electrode 42 of the controlling oxygen partial pressure-measuring cell 46 is composed of an inert material having a low catalytic activity on NOx such as NO contained in the measurement gas introduced into the gas sensor.

Especially, the inner pumping electrode 34 and the measuring electrode 42 may be composed of a porous cermet electrode. In this embodiment, the electrode is composed of a metal such as Pt and a ceramic such as $ZrO_2$. It is necessary to use a material which has a weak reducing ability or no reducing ability with respect to the NO component in the measurement gas, for the inner pumping electrode 34 and the measuring electrode 42 disposed in the first chamber 28 to make contact with the measurement gas. It is preferable that the inner pumping electrode 34 and the measuring electrode 42 are composed of, for example, a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

A detecting electrode 52 having a substantially rectangular planar configuration and composed of a porous cermet electrode is formed on an upper surface portion for forming the second chamber 30, of the upper surface of the first solid electrolyte layer 20d. An electrochemical pumping cell, i.e., a measuring pumping cell 54 is constructed by the detecting electrode 52, the inner pumping electrode 34 of the main pumping cell 38, the first solid electrolyte layer 20d, the second spacer layer 20e, and the second solid electrolyte layer 20f.

The detecting electrode 52 is composed of a porous cermet comprising Rh as a metal capable of reducing NOx as the measurement gas component and zirconia as a ceramic. Accordingly, the detecting electrode 52 functions as an NOx-reducing catalyst for reducing NOx existing in the atmosphere in the second chamber 30. Further, when a measuring voltage Vp2 is applied between the detecting electrode 52 and the inner pumping electrode 34 by the aid of a DC power source 56, the oxygen in the atmosphere in the second chamber 30 can be pumped out to the reference gas-introducing space 22. The pumping current Ip2, which flows in accordance with the pumping action of the measuring pumping cell 54, is detected by an ammeter 58.

The sensor element 12 further comprises a heater 60 for generating heat in accordance with electric power supply from the outside. The heater 60 is embedded in a form of being vertically interposed between the first and second substrate layers 20a, 20b. The heater 60 is provided in order to increase the conductivity of oxygen ion. A ceramic layer 62 composed of alumina or the like is formed to cover upper and lower surfaces of the heater 60 so that the heater 60 is electrically insulated from the substrate layers 20a, 20b.

As shown in FIG. 4, the heater 60 is arranged over the entire portion ranging from the first chamber 28 to the second chamber 30. Accordingly, each of the first chamber 28 and the second chamber 30 is heated to a predetermined temperature. Simultaneously, each of the main pumping cell 38, the controlling oxygen partial pressure-measuring cell 46, and the measuring pumping cell 54 is also heated to a predetermined temperature and maintained at that temperature.

The sensor element 12 is basically constructed as described above. Next, its function and effect will be explained.

Prior to the measurement of NOx, the sensor element 12 is set to be in a state in which the measurement gas can be introduced into the first chamber 28. Subsequently, an electric power is applied to the heater 60 to heat the first and second solid electrolyte layers 20d, 20f to desired states.

Next, the measurement gas is introduced into the sensor element 12 having been set as described above to start the measurement of NOx contained in the measurement gas.

The measurement gas is introduced into the first chamber 28 under the predetermined diffusion resistance through the first diffusion rate-determining section 24. The partial pressure of oxygen contained in the measurement gas is controlled to have a predetermined value in accordance with the predetermined pumping voltage Vp1 applied between the inner pumping electrode 34 and the outer pumping electrode 36 by the aid of the variable power source 40. That is, the partial pressure of oxygen in the first chamber 28 can be measured on the basis of the voltage V1 between the reference electrode 44 and the measuring electrode 42 detected by the voltmeter 48. The voltage V1 is the electromotive force of the oxygen concentration cell specified by the Nernst's equation described above. The voltage of the variable power source 40 is controlled so that the voltage V1 is, for example, not more than 300 mV. Thus, the partial pressure of oxygen in the first chamber 28 is controlled to have a predetermined value.

The measurement gas, which has been controlled to have the predetermined partial pressure of oxygen in the first chamber 28, is introduced into the second chamber 30 through the second diffusion rate-determining section 26.

In the second chamber 30, the predetermined pumping voltage Vp2, which makes it possible to sufficiently pump out $O_2$ in the second chamber 30, is applied between the detecting electrode 52 and the reference electrode 44 by the aid of the DC power source 56. NOx contained in the measurement gas is decomposed by the pumping voltage Vp2 or the NOx-decomposing catalyst disposed in the second chamber 30. $O_2$ generated thereby is pumped out toward the reference gas-introducing space 22 through the first solid electrolyte layer 20d. During this process, the current value Ip2, which is generated by the movement of oxygen ion, is measured by the ammeter 58. The concentration of the predetermined oxide, for example, NOx such as NO and $NO_2$ contained in the measurement gas is measured from the current value Ip2.

That is, when the voltage is applied to the oxygen ion-conductive solid electrolyte such as $ZrO_2$ (the first solid electrolyte layer 20d in the embodiment shown in FIG. 4), the current flows in accordance with the movement of oxygen ion. The current is measured as the pumping current Ip2 by the aid of the ammeter 58. In the case of a proton ion-conductive solid electrolyte, the current flows in accordance with the movement of proton.

Figure 5:
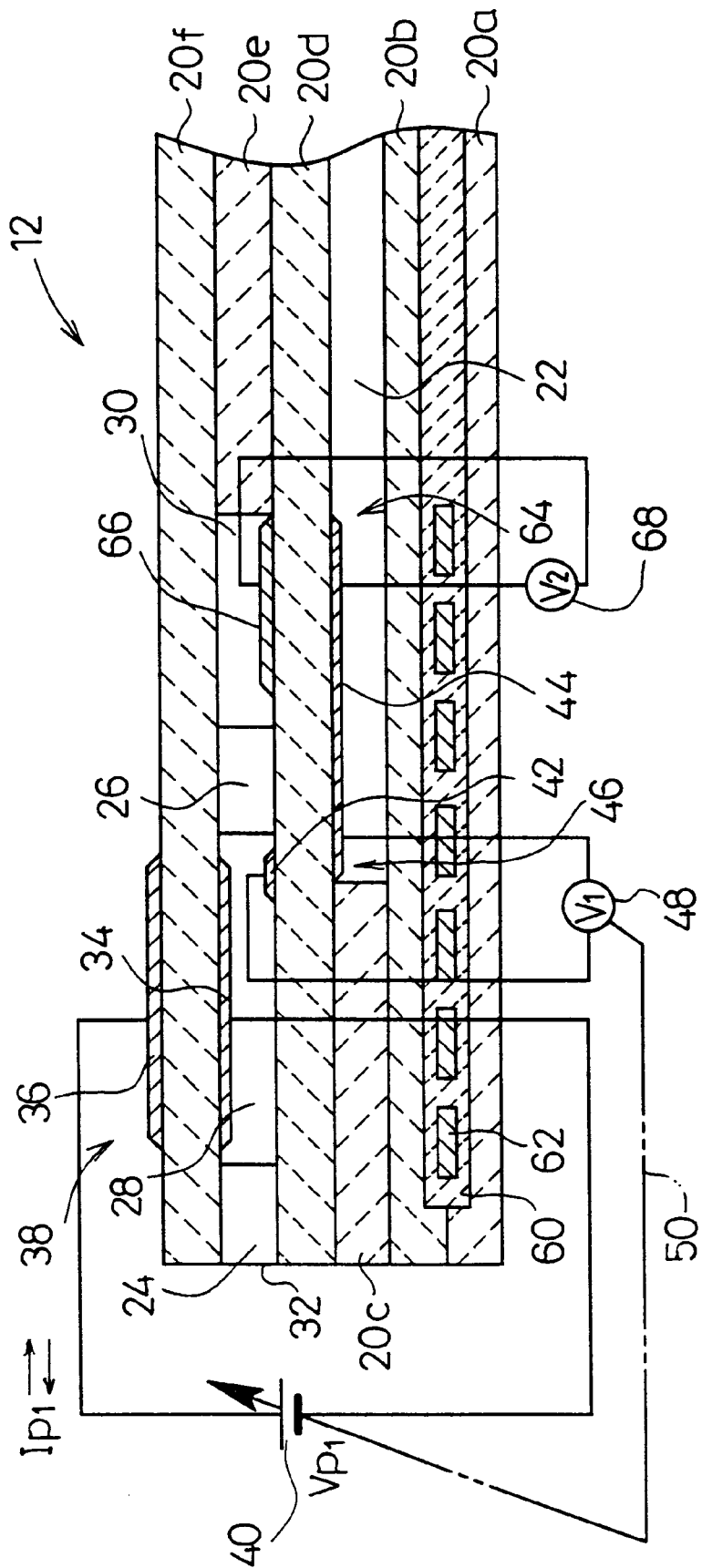
FIG. 5 shows a sectional view illustrating another arrangement of a gas sensor element.

Those other than the measuring pumping cell 54 may be used for the sensor element 12. That is, as shown in FIG. 5, a measuring oxygen partial pressure-measuring cell 64 may be used as the electrochemical sensor cell for detecting NOx, instead of the measuring pumping cell 54.

The measuring oxygen partial pressure-measuring cell 64 is constructed by a detecting electrode 66 formed on an upper surface portion for forming the second chamber 30, of the upper surface of the first solid electrolyte layer 20d, the reference electrode 44 formed on the lower surface of the first solid electrolyte layer 20d, and the first solid electrolyte layer 20d.

In this embodiment, an electromotive force (electromotive force of the oxygen concentration cell) V2, which corresponds to a difference in oxygen concentration between the atmosphere around the detecting electrode 66 and the atmosphere around the reference electrode 44, is generated between the detecting electrode 66 and the reference electrode 44 of the measuring oxygen partial pressure-measuring cell 64.

Therefore, the partial pressure of oxygen in the atmosphere around the detecting electrode 66, in other words, the partial pressure of oxygen defined by oxygen produced by reduction or decomposition of the measurement gas component (NOx) is detected as a voltage value V2 by measuring the electromotive force (voltage) V2 generated between the detecting electrode 66 and the reference electrode 44 by using a voltmeter 68.

The degree of change in the electromotive force V2 represents the NOx concentration. That is, the electromotive force V2, which is outputted from the measuring oxygen partial pressure-measuring cell 64 constructed by the detecting electrode 66, the reference electrode 44, and the first solid electrolyte layer 20d, represents the NOx concentration in the measurement gas.

As shown in FIG. 1A, the sensor element 12 is fixed by the sensor assembly 16. Specifically, the sensor element 12 is fixed by a housing 70 made of metal, a plurality of ceramic supporters 74a to 74c arranged in a hollow section of a cylindrical inner tube 72 secured by welding to the housing 70, and a ceramic powder 76 such as talc filled between the ceramic supporters 74a to 74c respectively. The sensor element 12 is enclosed in an air-tight manner by the ceramic powder 76.

In order to make electric connection between the sensor element 12 and the outside, for example, as shown in FIG. 1A, the gas sensor 10A according to the first embodiment includes an insert member 90 comprising a female contact 80 for making connection with a lead wire 78, a two-piece ceramic housing 82, a fixing metallic fixture 84, a press spring 86, and a caulking ring 88. The insert member 90 is inserted into an electrode terminal section 92 of the sensor element 12, and the outer circumference of the caulking ring 88 is caulked. Thus, the press spring 86 is displaced to press the female contact 80 against the electrode terminal section 92 with a predetermined force.

The structure and other features of the sensor assembly 16 are described in detail in Japanese Utility Model Publication Nos. 6-37325 and 6-37326 and Japanese Laid-Open Utility Model Publication No. 2-146362.

As shown in FIG. 1A, the protective cover 14 of the gas sensor 10A according to the first embodiment comprises an inner protective cover 110 and an outer protective cover 112 made of metal or synthetic resin.

The inner protective cover 110 has an opening section 114 disposed at its forward end for introducing the measurement gas. The opening section 114 has a rectangular pipe-shaped configuration having a predetermined length. An expanded section 118 having a predetermined height, which is wider in width than the opening section 114, is integrally formed at the back of the opening section 114 with an approximately rectangular step section 116 intervening therebetween. A cylindrical cover section 122 is integrally formed at the back of the expanded section 118 with a tapered step section 120 intervening therebetween. The cover section 122 has an outer diameter which is approximately the same as an inner diameter of a frontward hollow section of the housing 70. The cover section 122 has its rearward end which is folded outwardly to be interposed between a frontward surface of the ceramic supporter 74a of the sensor assembly 16 and a step surface of the hollow section of the housing 70 opposing thereto.

As indicated by a broken line in FIG. 2, the forward end surface of the sensor element 12 has a projected dimension which is larger than an aperture dimension of the opening section. The projected dimension is approximately the same as or slightly smaller than a projected dimension of a space defined and formed by an inner wall surface of the expanded section 118.

The dimension of the sensor element 12 is generally expressed as follows. That is, with reference to FIG. 3, the dimension in the longitudinal direction of the sensor element 12 is expressed as length, and the dimension in the transverse direction is expressed as width. With reference to FIG. 4, the dimension in the stacking direction of the solid electrolytes of the sensor element 12 is generally expressed as height. Therefore, in the following description, the dimension will be expressed in accordance with the general expression as described above.

The outer protective cover 112 is formed to have a cylindrical cap-shaped configuration with its tightly closed frontward portion and its open rearward portion. The inner diameter of the outer protective cover 112 is approximately the same as or slightly smaller than an outer diameter of a frontward small diameter section 124 of the housing 70 of the sensor assembly 16. The outer protective cover 112 is inserted into the small diameter section 124 of the housing 70 to be fixed by means of spot welding or the like so that the entire inner protective cover disposed at the inside is surrounded thereby. The outer protective cover 112 has a plurality of gas-introducing holes 126 which are formed through its side surface, for example, at an equal pitch.

As described above, the inner protective cover 110 is attached to surround the forward end of the sensor element 12, and the outer protective cover 112 is attached to surround the inner protective cover 110. Thus, a space (hereinafter referred to as "inner protective cover space") 130 is formed between the sensor element 12 and the inner protective cover 110. Further, a space (hereinafter referred to as "outer protective cover space") 132 is formed between the inner protective cover 110 and the outer protective cover 112.

In this embodiment, the inner dimension (i.e., the aperture dimension) of the opening section 114 (rectangular pipe) of the inner protective cover 110 is set to be larger than the dimension of the gas-introducing port 32 (see FIG. 3) of the sensor element 12. The gas diffusion resistance at the opening section 114 is set to be sufficiently lower than the gas diffusion resistance at the gas-introducing port 32 of the sensor element 12.

The dimension of the opening section 114 is about 3 mm in width d, about 0.8 mm in height h, and about 1.5 mm L in length. In other words, the opening section 114 is configured to have a communication passage 134 (see FIG. 1A) with a slit (aperture) 114a of 3 mm×0.8 mm formed to have the length of 1.5 mm. Therefore, condensed water hardly makes invasion. Even if condensed water makes invasion, the size of water droplets is extremely small. Therefore, even if condensed water contacts with the forward end of the sensor element 12, the thermal shock exerted thereby is extremely small. Accordingly, no crack is formed at the forward end of the sensor element 12.

The expanded section 118, which leads to the opening section 114, is provided for the purpose of positioning with respect to the opening section 114 and for the purpose of isolation of the inner protective cover space 130 from the outer protective cover space 132. When the forward end of the sensor element 12 is inserted along the inner wall surface of the expanded section 118, the position of the gas-introducing port 32 of the sensor element 12 is aligned with the position of the opening section 114 of the inner protective cover 110.

The abutment of the sensor element 12 against the step section 116 causes complete isolation of the inner protective cover space 130 from the outer protective cover space 132. Accordingly, the measurement gas, which diffuses and flows from the opening section 114 to the sensor element 12, does not enter the inner protective cover space 130. Therefore, the concentration of the predetermined gas component can be measured with good response performance by using the sensor element 12.

It is desirable that the ratio D1/D2 between the gas diffusion resistance D1 of the communication passage 134 and the gas diffusion resistance D2 from the inner protective cover space 130 to the communication passage 134 is set to be not more than ⅕. Even when the forward end of the sensor element 12 does not abut against the step section 116, the response delay, which would be otherwise caused by diffusion of gas into the inner protective cover space 130, is greatly improved provided that the gas diffusion resistance of the opening section 114 (gas diffusion resistance D1 of the communication passage 134) is not more than ⅕ of the gas diffusion resistance (gas diffusion resistance D2 from the inner protective cover space 130 to the communication passage 134) of the clearance between the sensor element 12 and the opening section 114.

If the opening section 114 communicates with the inner protective cover space 130, the diffused inflow measurement gas enters the inner protective cover space 130, because the inner protective cover space 130 has a large volume. In such a situation, the measurement gas which enters the sensor element 12 is decreased, and the response is delayed.

The side surface of the inner protective cover 110 has no hole for introducing the measurement gas. Therefore, the measurement gas does not directly contact with the sensor element 12. Accordingly, the sensor element 12 is not cooled by the measurement gas.

Since the inner protective cover 110 has the cylindrical configuration, a long distance is given between the side surface of the inner protective cover 110 and large surfaces (surfaces having large areas such as the upper and lower surfaces of the sensor element 12 in this embodiment) of the sensor element 12. Accordingly, even when the inner protective cover 110 is cooled by the measurement gas or the like, the thermal loss of the sensor element 12, which would be otherwise caused by heat radiation and heat convection, is decreased, because the distance between the inner protective cover 110 and the large surfaces of the sensor element 12 is long. That is, the sensor element 12 is structured to be hardly cooled.

As described above, the gas-introducing port 32 for introducing the measurement gas is not provided at the surface of the sensor element 12 (on the side of the large surface of the sensor element 12) opposing to the side surface of the inner protective cover 110. The gas-introducing port 32 is provided on the end surface side of the sensor element 12, and the opening section 114 of the inner protective cover 110 is allowed to directly communicate with the gas-introducing port 32 of the sensor element 12. Therefore, the sensor element 12 is hardly cooled, and the probability of adhesion of condensed water to the sensor element 12 is markedly small.

Even if condensed water adheres, the thermal shock can be extremely small, because the size of water droplets is extremely small. Therefore, no crack is formed in the sensor element 12, making it possible to simultaneously solve the problems of the element temperature drop and the crack formation caused by condensed water.

Even if oil combustion waste and carbon contained in the exhaust gas adhere to the opening section 114, and the gas diffusion resistance of the opening section 114 is increased, then it is possible to suppress the decrease in sensitivity and the decrease in response performance to the minimum, because the gas diffusion resistance of the opening section 114 is set to be sufficiently lower than the gas diffusion resistance of the sensor element 12.

Figure 1B:
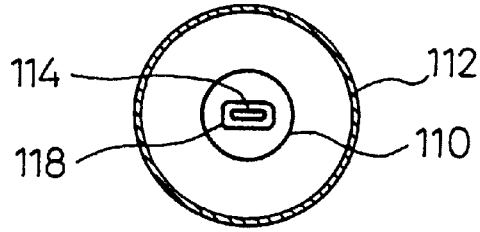
FIG. 1B shows a sectional view taken along a line IB—IB shown in FIG. 1A.

Next, a gas sensor 10B according to a second embodiment will be explained with reference to FIGS. 6A and 6B. Components or parts corresponding to those shown in FIGS. 1A and 1B are designated by the same reference numerals, duplicate explanation of which will be omitted.

Figure 6A:
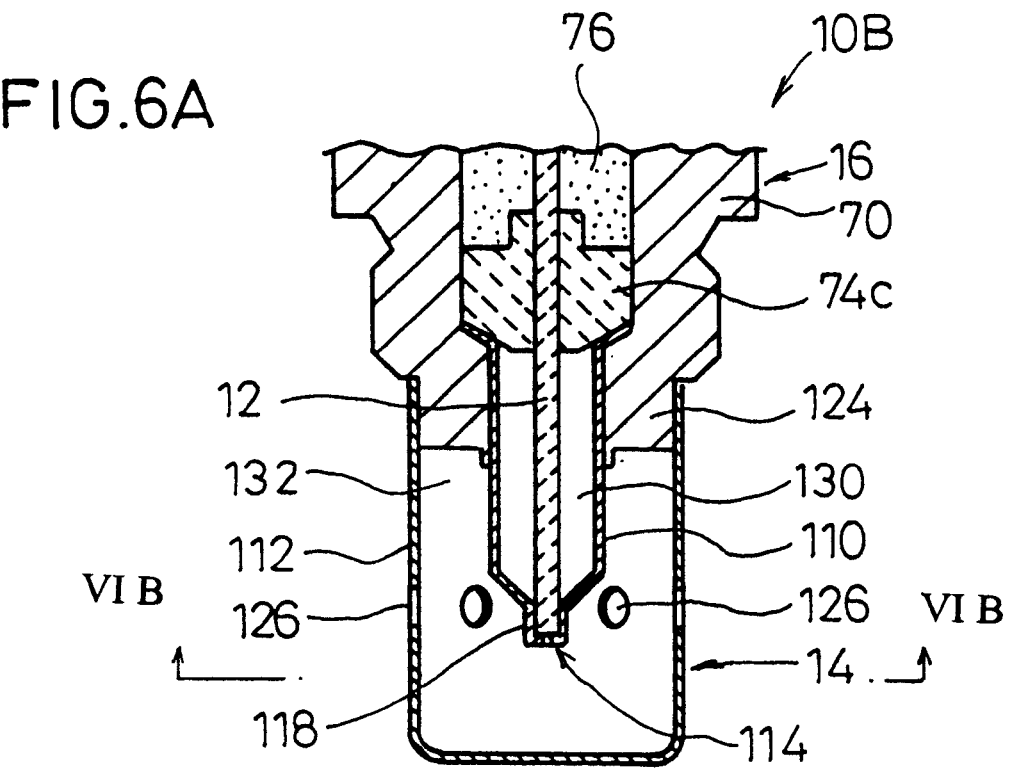
FIG. 6A shows, with partial omission, a sectional view illustrating principal parts of a gas sensor according to a second embodiment.
Figure 6B:
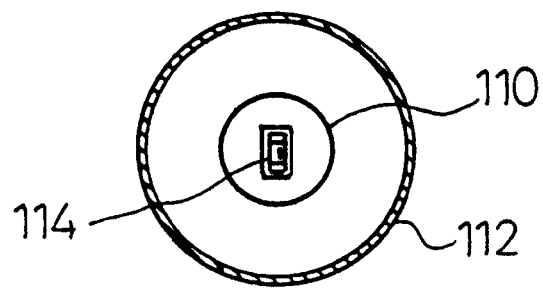
FIG. 6B shows a sectional view taken along a line VIB—VIB shown in FIG. 6A.

As shown in FIGS. 6A and 6B, the gas sensor 10B according to the second embodiment is constructed in approximately the same manner as the gas sensor 10A according to the first embodiment described above. However, in the gas sensor 10B, the opening section 114 of the inner protective cover 110 is not pipe-shaped, and the bottom surface of the inner protective cover 110 merely has a rectangular hole. The bottom section (forward end section) of the inner protective cover 110 has no step section, and it has a depressed configuration. The configuration of the opening section 114 is about 3 mm in width d, about 0.4 mm in height h, and 0.15 mm L in length (thickness of the inner protective cover 110).

Figure 7:
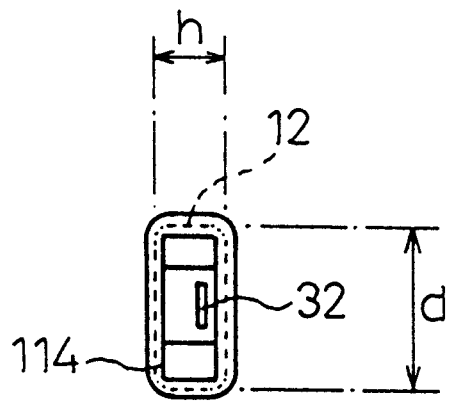
FIG. 7 shows a magnified view of principal parts illustrating a magnified opening section shown in FIG. 6B.

As shown by a broken line in FIG. 7, in the gas sensor 10B according to the second embodiment, the projected dimension of the forward end surface of the sensor element 12 is also larger than the dimension of the aperture (having a slit-shaped configuration) of the opening section 114, which is approximately the same as or slightly smaller than the projected dimension of the space defined and formed by the inner wall surface of the expanded section 118.

In this embodiment, although the length of the opening section 114 is 0.15 mm L which is shorter than 1.5 mm L of the gas sensor 10A according to the first embodiment, the height h is decreased from 0.8 mm to 0.4 mm. The probability of contact with water droplets is still extremely small as compared with the conventional protective cover (having holes through the side surface). Further, the size of water droplets is also small. Therefore, it is possible to effectively suppress occurrence of any crack in the sensor element 12.

The length of the opening section 114 is $1/10$, and the height h is $1/2$ as compared with the protective cover of the gas sensor 10A according to the first embodiment (see FIGS. 1A and 1B). Therefore, the ratio D1/D2 between the gas diffusion resistance D1 of the opening section 114 and the gas diffusion resistance D2 of the clearance of the opening section 114 is further decreased by $1/5$ as compared with the gas sensor 10A according to the first embodiment. Accordingly, the gas sensor 10B according to the second embodiment is advantageous in response performance.

In the gas sensor 10B according to the second embodiment, the isolation of the inner protective cover space 130 from the outer protective cover space 132 and the positional adjustment between the gas-introducing port 32 of the sensor element 12 and the opening section 114 are also ensured by inserting the sensor element 12 into the depressed section (expanded section 118) formed at the bottom of the inner protective cover 110.

Next, a gas sensor 10C according to a third embodiment will be explained with reference to FIGS. 8A to 9. Components or parts corresponding to those shown in FIGS. 6A and 6B are designated by the same reference numerals, duplicate explanation of which will be omitted.

Figure 8A:
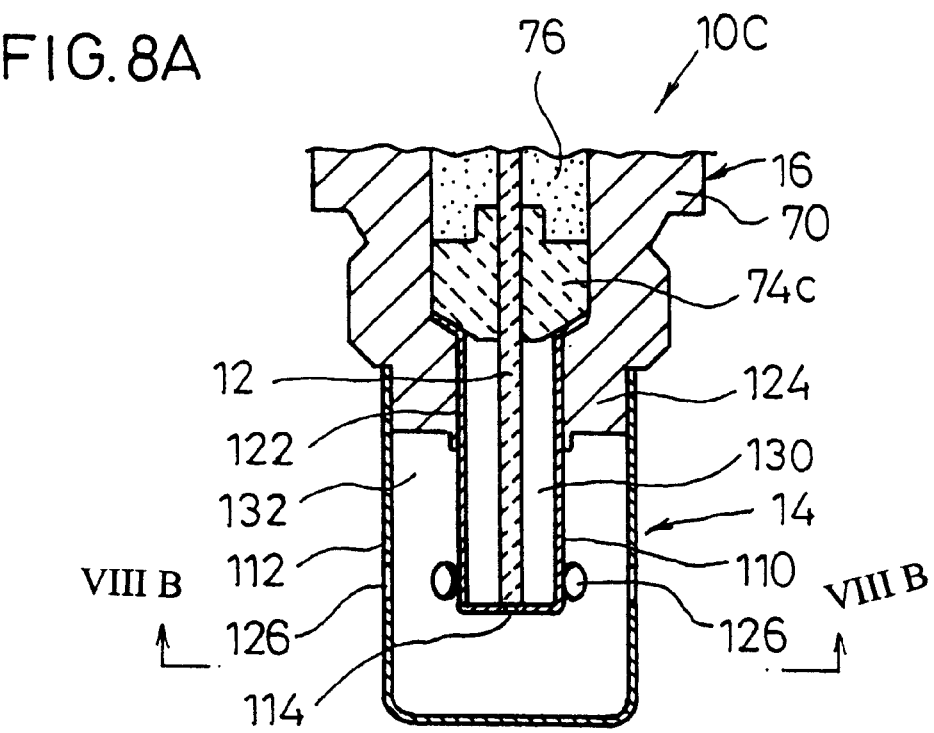
FIG. 8A shows, with partial omission, a sectional view illustrating principal parts of a gas sensor according to a third embodiment.
Figure 8B:
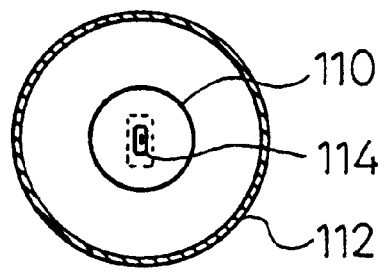
FIG. 8B shows a sectional view taken along a line VIIIB—VIIIB shown in FIG. 8A.
Figure 9:
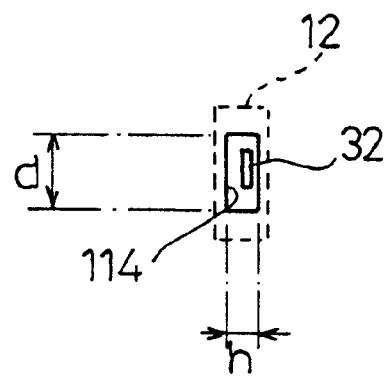
FIG. 9 shows a magnified view of principal parts illustrating a magnified opening section shown in FIG. 8B.

As shown in FIGS. 8A and 8B, the gas sensor 10C according to the third embodiment is constructed in approximately the same manner as the gas sensor 10B according to the second embodiment described above (see FIGS. 6A and 6B). However, the former is different from the latter in that the inner protective cover 110 includes no step section. That is, the inner protective cover 110 of the gas sensor 10C according to the third embodiment includes neither step section nor expanded section 118. The entire inner protective cover 110 is structured as a cover section 122 with an opening section 114 formed at its flat bottom portion. In the gas sensor 10C according to the third embodiment, as shown by a broken line in FIG. 9, the projected dimension of the forward end surface of the sensor element 12 is set to be larger than the dimension of the aperture (having a slit-shaped configuration) of the opening section 114.

The step section is provided for the purpose of the positional adjustment between the gas-introducing port 32 of the sensor element 12 and the opening section 114 of the inner protective cover 110 and the isolation of the inner protective cover space 130 from the outer protective cover space 132 as described above. However, as shown in FIGS. 8A and 8B, the purpose can be achieved by merely allowing the forward end surface of the sensor element 12 to abut against the bottom surface of the inner protective cover 110, even when the step section as described above is not provided. In this embodiment, the dimension of the opening section 114 of the inner protective cover 110 may be set to have a size in consideration of dispersion of the assembly position of the sensor element 12.

In the gas sensor 10C according to the third embodiment, the positional dispersion is ±0.3 mm at the forward end of the sensor element 12. Therefore, the dimension of the opening section 114 is set to be 0.6 mm×2.0 mm with respect to the size (0.15 mm×0.5 mm) of the gas-introducing port 32 of the sensor element 12. Even when the position of the sensor element 12 is dispersed, there is no change in the ratio between the gas diffusion resistance of the opening section 114 and the gas diffusion resistance of the sensor element 12.

Next, a gas sensor 10D according to a fourth embodiment will be explained with reference to FIGS. 10A to 11. Components or parts corresponding to those shown in FIGS. 1A and 1B are designated by the same reference numerals, duplicate explanation of which will be omitted.

Figure 10A:
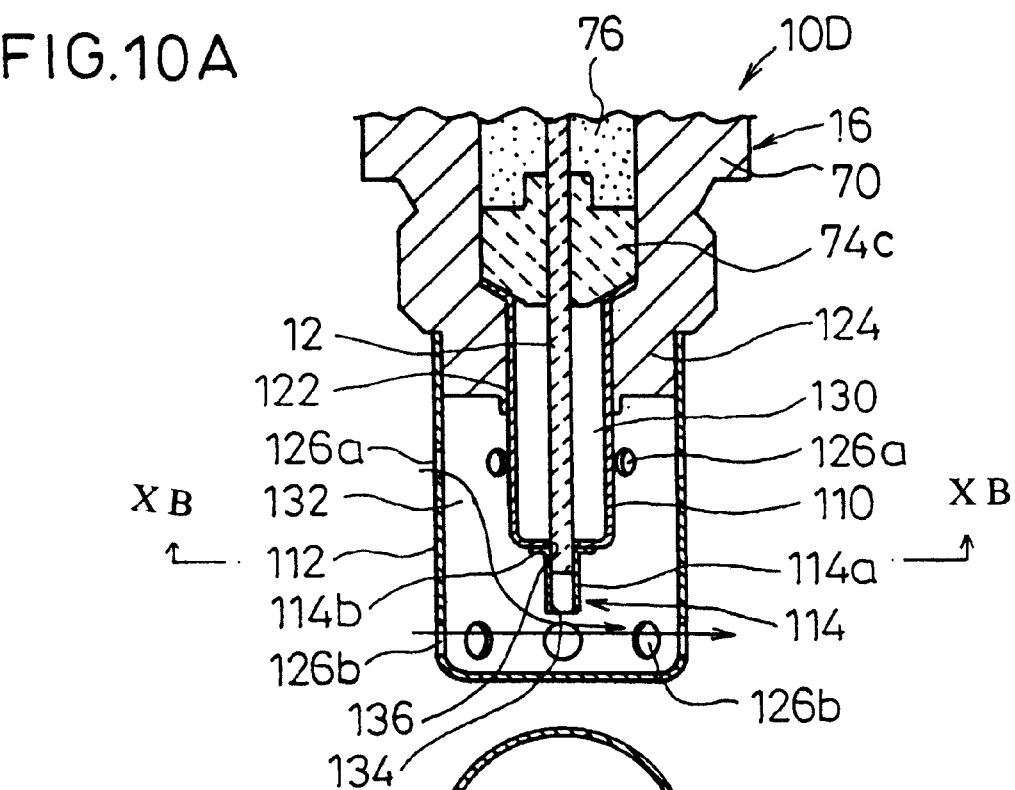
FIG. 10A shows, with partial omission, a sectional view illustrating principal parts of a gas sensor according to a fourth embodiment.
Figure 10B:
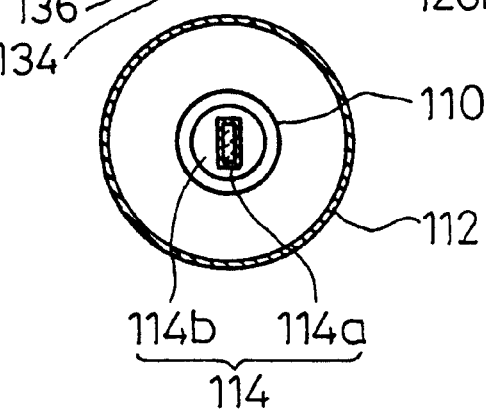
FIG. 10B shows a sectional view taken along a line XB—XB shown in FIG. 10A.

As shown in FIGS. 10A and 10B, the gas sensor 10D according to the fourth embodiment is constructed in approximately the same manner as the gas sensor 10A according to the first embodiment described above (see FIGS. 1A and 1B). However, the former is different from the latter in that an opening section 114 of the inner protective cover 110 is composed of a different member, and that two arrays of gas-introducing holes 126 are formed through the side surface of the outer protective cover 112. The two arrays of gas-introducing holes 126 are arranged as follows. That is, the upper gas-introducing holes 126a are composed of six individuals of 2 mm$\phi$ holes which are equally spaced apart from each other. The lower gas-introducing holes 126b are composed of eight individuals of 2.5 mm$\phi$ holes which are equally spaced apart from each other.

The entire inner protective cover 110 is formed as a cover section 122 in the same manner as the gas sensor 10C according to the third embodiment shown in FIG. 8A, which is structured such that a through-hole 136 is formed at a flat portion at its bottom.

The opening section 114, which is composed of the different member, includes a main opening body section 114a having a rectangular pipe-shaped configuration, and a flange section 114b for fixing the main opening body section 114a to the outer bottom surface of the inner protective cover 110. The length of the opening section 114 is about 2.0 mm.

The opening section 114 is fixed to the inner protective cover 110 as follows. That is, the opening section 114 is attached to the inner protective cover 110 by assembling the inner protective cover 110 to the sensor assembly 16, thereafter inserting the main opening body section 114a composed of the different member into the forward end section of the sensor element 12 protruding outwardly from the bottom of the inner protective cover 110, and fixing the flange section 114b to the outer bottom surface of the inner protective cover 110, for example, by means of welding. After that, the outer protective cover 112 is inserted into the small diameter section 124 of the housing 70, followed by being fixed by welding.

Figure 11:
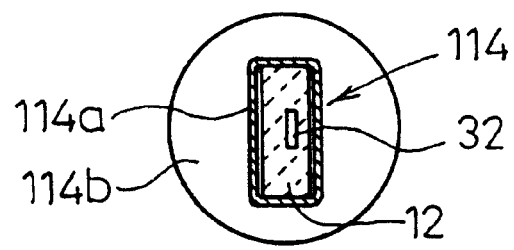
FIG. 11 shows a magnified view of principal parts illustrating a magnified opening section shown in FIG. 10B.

As shown in FIG. 11, for example, the opening section 114 has its inner dimension to give a clearance of 0.05 mm on one side with respect to the outer dimension of the sensor element 12, and it is positioned closely adjacent to the sensor element 12 over a length of 1.5 mm.

The outer dimension of the sensor element 12 is 4.2 mm×1.2 mm. The gas diffusion resistance (1/D)×(L/S) of the closely adjacent portion is as follows:

$$(1/D) \times (1.5/((4.2+1.2+4.2+1.2)\times 0.05)) = 2.78/D$$

wherein D represents the diffusion coefficient of the measurement gas.

On the other hand, the inner dimension of the opening section 114 resides in a configuration in which a slit of 4.3 mm×1.3 mm is formed over a length of 2.0 mm. The gas diffusion resistance (1/D)×(L/S) is as follows:

$$(1/D) \times (2.0/(4.3 \times 1.3)) = 0.36/D$$

The gas diffusion resistance ratio is 2.78D/0.36D≈7.7. The gas diffusion resistance from the inner protective cover 110 to the sensor element 12 is set to be approximately 8-fold. Therefore, almost all of the measurement gas enters the sensor element 12, and the measurement gas scarcely enters the inner protective cover space 130. The inner protective cover space 130 is substantially isolated from the outer protective cover space 132.

According to this structure, the positional dispersion of the sensor element 12 can be easily dissolved, because the opening section 114 is composed of the different member. Further, it is possible to set, for example, the length and the aperture area of the opening section 114 without restraint. Accordingly, the degree of freedom of design of the opening section 114 is increased. For example, the length can be increased without increasing the gas diffusion resistance by increasing the aperture area of the inlet portion of the opening section 114 and increasing the length of the opening section 114. Thus, it is possible to further decrease the probability of adhesion of condensed water.

It is possible to design and manufacture the gas sensor so that the gas diffusion resistance of the isolation space (gap portion between the sensor element 12 and the opening section 114) also has a sufficiently large value.

On the other hand, the gas-introducing holes 126 of the outer protective cover 112 are formed in two arrays as described above. The upper gas-introducing holes 126a are composed of six individuals of 2 mm$\phi$ holes which are equally spaced apart from each other. The lower gas-introducing holes 126b are composed of eight individuals of 2.5 mm$\phi$ holes which are equally spaced apart from each other.

Accordingly, the measurement gas (exhaust gas) flows vertically downwardly as shown by an arrow in FIG. 10A. There is hardly caused adhesion of particles such as oil combustion waste and carbon to the inlet portion of the opening section 114.

It is noted that the gas flow rate in the exhaust pipe has a distribution in which the gas flow rate is fast at the center, and it is slow at portions deviated in the direction toward the inner wall surface. Therefore, the flow rate of gas passing through the lower gas-introducing holes 126b is faster than the flow rate of gas passing through the upper gas-introducing holes 126a shown in FIG. 10A, giving a negative pressure. Accordingly, a flow of gas appears in a direction from the upper gas-introducing holes 126a to the lower gas-introducing holes 126b. Further, in the embodiment shown in FIG. 10A, the diameter as well as the number of the upper gas-introducing holes 126a is decreased as compared with the diameter of the lower gas-introducing holes 126b. Therefore, the gas flow directed in the downward direction is effectively produced. That is, the lower gas-introducing holes 126b function as gas discharge holes.

Next, a gas sensor 10E according to a fifth embodiment will be explained with reference to FIGS. 12A to 13. Components or parts corresponding to those shown in FIGS. 10A and 10B are designated by the same reference numerals, duplicate explanation of which will be omitted.

Figure 12A:
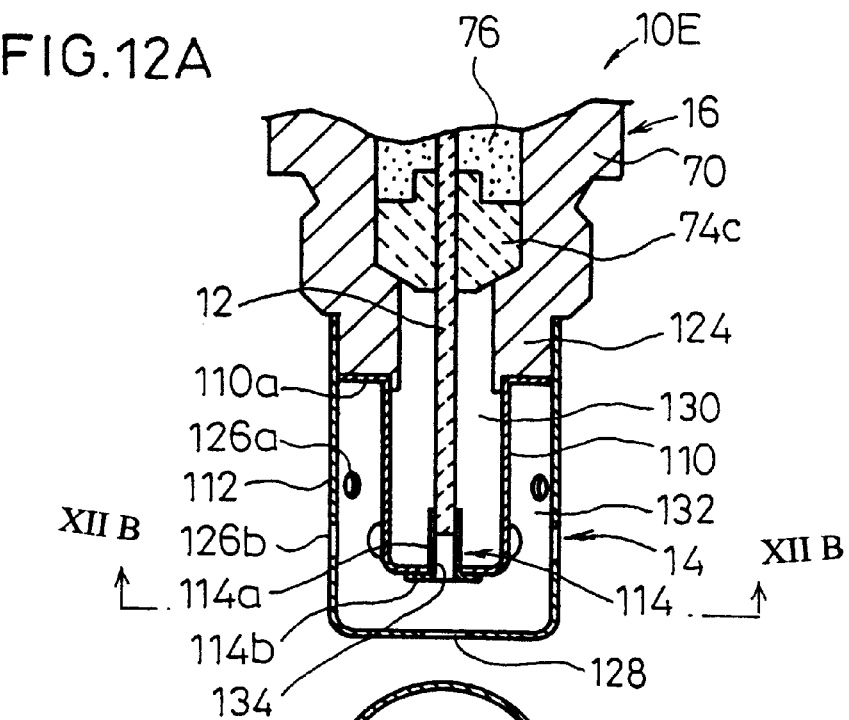
FIG. 12A shows, with partial omission, a sectional view illustrating principal parts of a gas sensor according to a fifth embodiment.
Figure 12B:
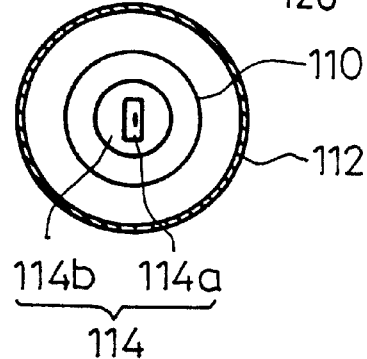
FIG. 12B shows a sectional view taken along a line XIIB—XIIB shown in FIG. 12A.
Figure 13:
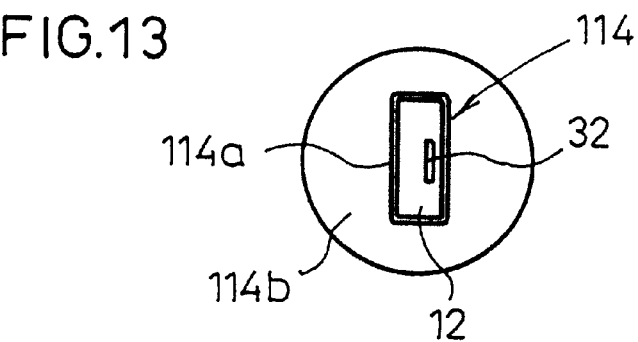
FIG. 13 shows a magnified view of principal parts illustrating a magnified opening section shown in FIG. 12B.

As shown in FIGS. 12A, 12B, and 13, the gas sensor 10E according to the fifth embodiment is constructed in approximately the same manner as the gas sensor 10D according to the fourth embodiment described above. However, the former is different from the latter in the following points.

That is, the forward end of the sensor element 12 is arranged at a position deeper than the bottom of the inner protective cover 110, and an opening section 114 composed of a different member is attached between a through-hole (not shown) of the inner protective cover 110 and the forward end of the sensor element 12. In other words, the opening section 114 is provided in an opposite direction as compared with the gas sensor 10D according to the fourth embodiment (see FIGS. 10A and 10B).

The inner protective cover 110 has a large diameter as a whole, with a flange section 110*a* disposed at its backward end (end portion on the side of the housing). The flange section 110*a* is fixed to the bottom surface of the housing 70 by means of, for example, projection welding. Gas-introducing holes 126 (upper gas-introducing holes 126*a* and lower gas-introducing holes 126*b*) of the outer protective cover 112 are generally disposed on the side of the housing 70. A gas discharge hole 128 is formed through the bottom (front section) of the outer protective cover 112.

The inlet portion of the opening section 114 can be set at an upward position by arranging the opening section 114 in the opposite direction, making it possible to elongate the distance to the outer protective cover 112. Accordingly, the condensed water, which would be otherwise stored due to the surface tension, is hardly stored between the opening section 114 and the outer protective cover 112. Further, it is possible to decrease the probability of arrival at the opening section 114, of condensed water scattered and entered via the gas discharge hole 128 provided through the bottom of the outer protective cover 112.

The lower gas-introducing holes 126*b* of the outer protective cover 112 are disposed at the positions opposing to the side surface of the inner protective cover 110. Therefore, the condensed water, which is scattered and entered via the gas-introducing holes (upper gas-introducing holes 126*a* and lower gas-introducing holes 126*b*) of the outer protective cover 112, hardly contacts with the opening section 114, providing an effect that the probability of adhesion to the sensor element 12 is further decreased.

The opening section 114 is not directly exposed to the atmosphere of the measurement gas. Therefore, particles such as oil combustion waste are hardly stored in the opening section 114.

The gas discharge hole 128 is provided through the bottom of the outer protective cover 112. Therefore, the gas flow rate is fast at the outer surface of the outer protective cover 112, giving a negative pressure. Accordingly, a flow of the measurement gas, which is directed vertically downwardly, is produced. Thus, it is possible to effectively decrease the adhesion of particles such as oil combustion waste and the adhesion of condensed water.

Since the inner protective cover 110 has a large inner diameter, it is possible to suppress the element temperature drop which would be otherwise caused, for example, by heat radiation and convection from the sensor element 12.

Next, a gas sensor l0F according to a sixth embodiment will be explained with reference to FIGS. 14A to 15. Components or parts corresponding to those shown in FIGS. 1A and 1B are designated by the same reference numerals, duplicate explanation of which will be omitted.

Figure 14A:
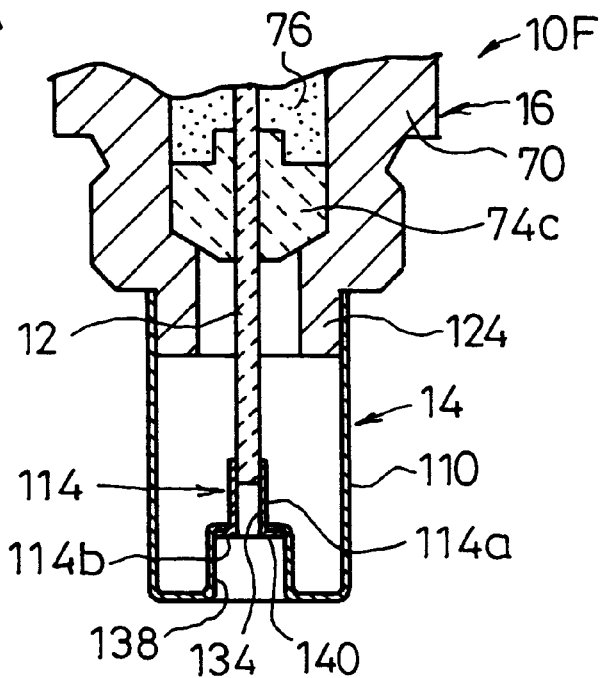
FIG. 14A shows, with partial omission, a sectional view illustrating principal parts of a gas sensor according to a sixth embodiment.
Figure 14B:
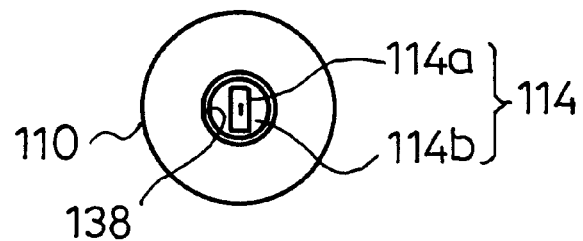
FIG. 14B shows a front view as viewed from a side of an opening section shown in FIG. 14A.
Figure 15:
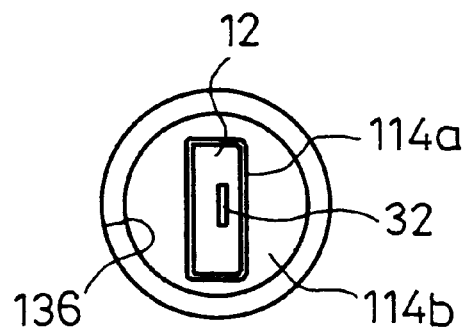
FIG. 15 shows a magnified view of principal parts illustrating the magnified opening section shown in FIG. 14B.

As shown in FIGS. 14A, 14B, and 15, the gas sensor 10F according to the sixth embodiment is different from the gas sensors according to the foregoing embodiments (gas sensors 10A to 10E according to the first to fifth embodiments), which is characterized in that the protective cover is constructed by only an inner protective cover 110, and there is no outer protective cover 112.

In this embodiment, the inner protective cover 110 is formed to have an approximately cylindrical cap-shaped configuration with a recess 138 having a predetermined diameter and formed at its frontward central portion (central portion of the bottom), and with its backward end which is open. The inner diameter of the inner protective cover 110 is approximately the same as or slightly smaller than the outer diameter of the frontward small diameter section 124 of the housing 70 of the sensor assembly 16. The sensor element 12, which is arranged at the inside, is surrounded by the inner protective cover 110 by inserting it into the small diameter section 124 of the housing 70 to make fixation.

The sensor element 12 has its forward end which is arranged at a position deeper than the bottom of the inner protective cover 110 (bottom of the recess 138 in this embodiment) in the same manner as the gas sensor 10E according to the fifth embodiment. An opening section 114, which is composed of a different member, is fixed by means of, for example, welding between a through-hole 140 formed at the bottom center of the recess 138 and the forward end of the sensor element 12.

In the gas sensor 10F according to the fifth embodiment, the protective cover has the single structure including only the inner protective cover 110. Therefore, it is feared that the element temperature drop may occur due to exhaust gas which may directly contact with the inner protective cover 110. However, the inner diameter of the inner protective cover 110 is largest among the inner protective covers 110 of the gas sensors 10A to 10E according to the foregoing embodiments. Therefore, the gas sensor 10F according to the fifth embodiment has the structure in which the element temperature drop, which would be otherwise caused by heat radiation and convection, is suppressed.

In the gas sensor 10F according to the sixth embodiment, the inner protective cover 110 is provided with the recess 138 at its bottom, having the structure in which the opening section 114 is fixed to the recess 138. Therefore, the inflow passage of the measurement gas has its cross-sectional area which is large in the vicinity of the inlet of the recess 138 and which is narrow at the opening section 114. Further, the inflow passage is long as a whole. Accordingly, the gas diffusion resistance at the opening section 114 is maintained to be lower than the gas diffusion resistance at the gas-introducing port 32 of the sensor element 12, in the same manner as the gas sensors 10A to 10E according to the first to fifth embodiments.

As described above, the distance from the vicinity of the inlet of the recess 138 to the sensor element 12 is long. Therefore, condensed water hardly makes contact to that extent. Further, since the opening section 114 is arranged at the deep portion of the recess 138, the gas sensor 10F according to the sixth embodiment has the feature that particles such as oil combustion waste hardly adhere to the opening section 114.

In other words, the gas sensor 10F according to the sixth embodiment functions as follows. That is, although the protective cover 14 has the simple structure, i.e., the single structure, there are provided the countermeasure against condensed water and the countermeasure against the element temperature drop, while maintaining good response performance. Moreover, the gas sensor 10F hardly suffers from the influence of adhesion of particles such as oil combustion waste and carbon.

Next, a gas sensor 10G according to a seventh embodiment will be explained with reference to FIGS. 16A to 17. Components or parts corresponding to those shown in FIGS. 12A and 12B are designated by the same reference numerals, duplicate explanation of which will be omitted.

Figure 16A:
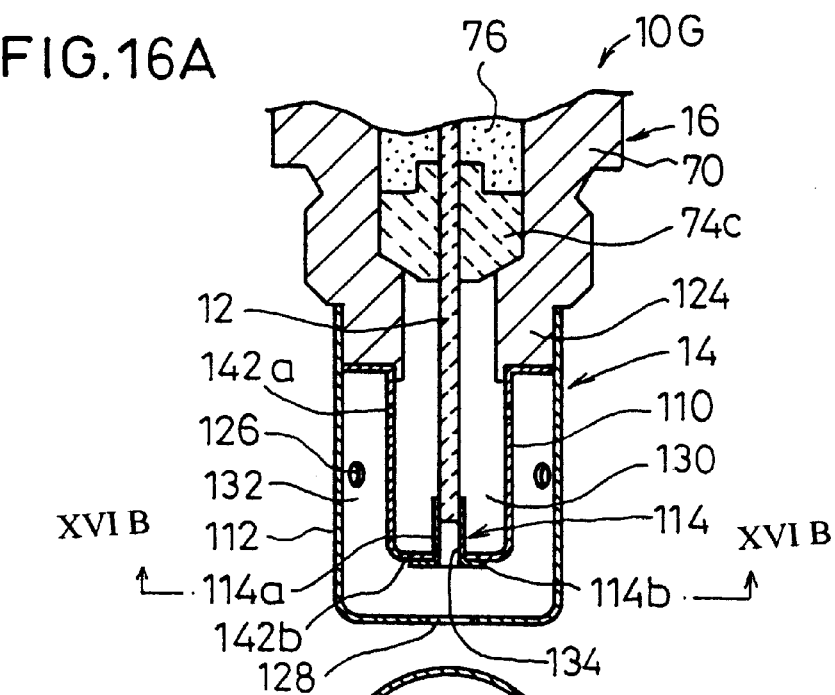
FIG. 16A shows, with partial omission, a sectional view illustrating principal parts of a gas sensor according to a seventh embodiment.
Figure 16B:
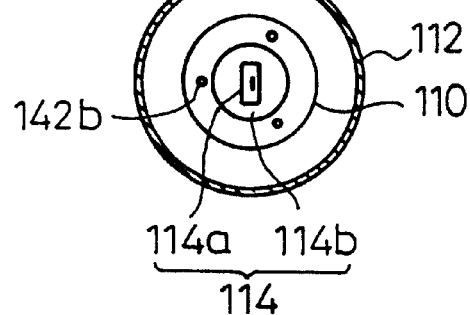
FIG. 16B shows a sectional view taken along a line XVIB—XVIB shown in FIG. 16A.
Figure 17:
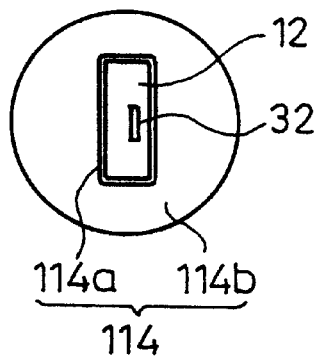
FIG. 17 shows a magnified view of principal parts illustrating a magnified opening section shown in FIG. 16B.

As shown in FIGS. 16A, 16B and 17, the gas sensor 10G according to the seventh embodiment is constructed in approximately the same manner as the gas sensor 10E according to the fifth embodiment described above (see FIGS. 12A and 12B). However, the former is different from the latter in that four individuals of 0.5 mmϕ holes (side holes 142a) are provided through the side surface of the inner protective cover 110, and they are equally spaced apart from each other, and that three individuals of 0.5 mmϕ holes (bottom holes 142b) are also provided through the bottom surface of the inner protective cover 110, and they are equally spaced apart from each other.

The gas sensor 10G according to the seventh embodiment is effective when there is no sufficient ratio D1/D2 between the gas diffusion resistance D1 of the communication passage 134 and the gas diffusion resistance D2 from the inner protective cover space 130 to the communication passage 134, or when there is no sufficient ratio D1/D2 between the gas diffusion resistance D1 of the opening section 114 and the gas diffusion resistance D2 of the clearance between the sensor element 12 and the opening section 114 (hereinafter simply referred to as "isolation gas diffusion resistance ratio").

That is, even when the isolation gas diffusion resistance ratio D1/D2 is small, it is possible to avoid any delay of response, because the gas sensor 10G has the structure in which the measurement gas also enters the inner protective cover space 130. The side holes 142a and the bottom holes 142b, which are provided through the side surface and the bottom surface of the inner protective cover 110, are 0.5 mmϕ and small respectively. Thus, the influence on the element temperature drop is decreased.

As for condensed water, both of the side holes 142a and the bottom holes 142b are disposed at the positions deviated from the gas-introducing holes 126 and the gas discharge hole 128 of the outer protective cover 112, and they are small holes of 0.5 mmϕ. Therefore, water droplets hardly contact with the sensor element 12, as well as they are small in size. Accordingly, it is possible to mitigate the thermal shock which may be exerted on the sensor element 12.

As described above, the gas sensors 10A to 10G according to the first to seventh embodiments make it possible to simultaneously provide the countermeasure against the condensed water, the countermeasure against the element temperature drop, and the countermeasure against the decrease in response performance caused by adhesion of particles, while ensuring the response performance.

In the case of the automobiles, for example, the following environment is given. That is, condensed water is produced, the gas flow rate greatly varies in a range from the low speed to the high speed, and thus the environment concerning the element temperature drop greatly varies. Additionally, for example, particles such as oil combustion waste and carbon come to the gas sensor. Even in the severe environment for various types of sensors, the present invention makes it possible to suppress the influence exerted thereby to the minimum, which is extremely effective from the industrial viewpoint.

In the gas sensors 10A to 10G according to the first to seventh embodiments described above, the isolation space between the inner protective cover space 130 and the communication passage 134 may be filled with a heat-resistant filler such as glass, ceramic cement, glass wool, and metal mesh (obtained by pressing and hardening metal wire). In this embodiment, it is possible to further decrease the isolation gas diffusion resistance ratio.

When the aperture width of the opening section 114 is large, the opening section 114 may be filled with a porous material. In this embodiment, the opening section 114 may be filled with, for example, porous metal, metal mesh, porous ceramic, and glass wool. Accordingly, it is possible to further decrease the probability that condensed water will contact with the sensor element.

It is a matter of course that the gas sensor according to the present invention is not limited to the foregoing embodiments, which may be constructed in other various forms without deviating from the gist or essential characteristics of the present invention.

As explained above, the present invention provides the gas sensor comprising the sensor element for measuring the predetermined gas component contained in the introduced measurement gas, and the protective cover arranged to surround the sensor element. The gas sensor includes the sensor element having the gas-introducing port which is disposed at the forward end surface thereof for introducing the measurement gas thereinto; the protective cover having the opening section which makes communication with the gas-introducing port; and the protective cover space formed between the protective cover and the sensor element, the protective cover space being isolated from the communication passage which makes communication between the opening section of the protective cover and the gas-introducing port of the sensor element. The measurement gas principally diffuses and flows from the opening section into the gas-introducing port of the sensor element.

Accordingly, the effect is obtained, i.e., it is possible to simultaneously solve the element temperature drop and the crack formation caused by condensed water, and highly accurately measure the predetermined gas component.

What is claimed is:

1. A gas sensor comprising a sensor element for continuously measuring a predetermined gas component contained in an introduced measurement gas, and a protective cover arranged to surround said sensor element, said gas sensor including:

said sensor element having a gas-introducing port which is disposed at a forward end surface thereof for introducing said measurement gas there into;

said protective cover having an opening section which makes fluid communication with said gas-introducing port; and a protective cover space formed between said protective cover and said sensor element, said protective cover space being isolated by an isolation space from a communication passage which makes fluid communication from said opening section of said protective cover to said gas-introducing port of said sensor element, wherein:

said measurement gas principally diffuses and flows from said opening section into said gas-introducing port of said sensor, providing improved resistance against water invasion, thermal shock, and/or crack formation, element.

2. The gas sensor according to claim 1, wherein assuming that a gas diffusion resistance of said communication passage is D1, and a gas diffusion resistance from said protective cover space to said communication passage is D2, a ratio D1/D2 between said gas diffusion resistances is not more than ⅕.

3. The gas sensor according to claim 1, wherein a hole for making fluid communication for at least said measurement gas with said protective cover space is provided through a side surface and/or a bottom surface of said protective cover.

4. The gas sensor according to claim 1, wherein:

assuming that a gas diffusion resistance of said communication passage is D1, and a gas diffusion resistance from said protective cover space to said communication passage is D2, a ratio D1/D2 between said gas diffusion resistances is not more than 1/5; and said end surface of said sensor element abuts against said protective cover.

5. The gas sensor according to claim 1, wherein:

a hole for making fluid communication for at least said measurement gas with said protective cover space is provided through a side surface and/or a bottom surface of said protective cover; and said isolation space is filled with a filler.

6. The gas sensor according to claim 1, further comprising an outer protective cover disposed to surround said protective cover and provided with at least a gas-introducing hole.

7. The gas sensor according to claim 6, wherein a gas discharge hole for said measurement gas is provided through a bottom of said outer protective cover.

8. The gas sensor according to claim 7, wherein a plurality of gas discharge holes each having a diameter of not more than 2 mm are provided through said bottom of said outer protective cover.

9. The gas sensor according to claim 6, wherein:

a gas discharge hole for said measurement gas is provided through a bottom of said outer protective cover; and said gas discharge hole is provided at a position not opposing to said opening section.

10. The gas sensor according to claim 1, wherein a gas diffusion resistance of said opening section is not more than 1/10 of a gas diffusion resistance of said sensor element.

11. The gas sensor according to claim 1, wherein a length of said opening section in a direction to extend toward said sensor element is not less than 1.5-fold of an aperture width of said opening section.

12. The gas sensor according to claim 1, wherein an aperture of said opening section has a slit-shaped configuration of not more than 1 mm.

13. The gas sensor according to claim 1, wherein said opening section is filled with a porous material.

14. The gas sensor according to claim 1, wherein:

a gas diffusion resistance of said opening section is not more than 1/10 of a gas diffusion resistance of said sensor element; and said opening section is composed of a member which is different from that for said protective cover.

15. The gas sensor according to claim 14, wherein:

a recess is provided at a bottom of said protective cover; and said opening section is provided at said recess.

* * * * *

UNITED STATES PATENT AND TRADEMARK OFFICE
CERTIFICATE OF CORRECTION

PATENT NO. : 5,948,963
DATED : September 7, 1999
INVENTOR(S) : Nobuhide KATO et al.

It is certified that error appears in the above-indentified patent and that said Letters Patent is hereby corrected as shown below:

Column 20, line 31, in Claim 1, after "sensor" (first occurrence) insert --, providing improved resistance against water invasion, thermal shock, and/or crack formation,--;

Column 20, lines 52-54, in Claim 1, after "sensor" delete ", providing improved resistance against water invasion, thermal shock, and/or crack formation,".

Signed and Sealed this

Twenty-third Day of May, 2000

Attest:

Q. TODD DICKINSON

*Attesting Officer*     *Director of Patents and Trademarks*